United States Patent
Trieu

(10) Patent No.: US 7,758,644 B2
(45) Date of Patent: Jul. 20, 2010

(54) SYSTEMS AND TECHNIQUES FOR INTRAVERTEBRAL SPINAL STABILIZATION WITH EXPANDABLE DEVICES

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1202 days.

(21) Appl. No.: 10/717,693

(22) Filed: Nov. 20, 2003

(65) Prior Publication Data

US 2004/0102774 A1    May 27, 2004

Related U.S. Application Data

(60) Provisional application No. 60/428,081, filed on Nov. 21, 2002.

(51) Int. Cl.
*A61F 2/44* (2006.01)
(52) U.S. Cl. .................................. 623/17.11
(58) Field of Classification Search ... 623/17.11–17.16; 606/60, 61
See application file for complete search history.

(56) References Cited

U.S. PATENT DOCUMENTS

| | | |
|---|---|---|
| 3,875,595 A | 4/1975 | Froning |
| 4,772,287 A | 9/1988 | Ray et al. |
| 4,863,477 A | 9/1989 | Monson |
| 4,932,969 A | 6/1990 | Frey et al. |
| 4,969,888 A | 11/1990 | Scholten et al. |
| 5,002,576 A | 3/1991 | Fuhrmann et al. |
| 5,059,193 A | 10/1991 | Kuslich |
| 5,108,404 A | 4/1992 | Scholten et al. |
| 5,123,926 A | 6/1992 | Pisharodi |
| 5,171,278 A | 12/1992 | Pisharodi |
| 5,236,460 A | 8/1993 | Barber |
| 5,390,683 A | 2/1995 | Pisharodi |
| 5,423,850 A | 6/1995 | Berger |
| 5,480,400 A | 1/1996 | Berger |
| 5,549,679 A | 8/1996 | Kuslich |
| 5,645,597 A | 7/1997 | Krapiva |
| 5,785,647 A | 7/1998 | Tompkins et al. |
| 5,800,550 A * | 9/1998 | Sertich ..................... 623/17.16 |
| 5,827,289 A | 10/1998 | Reiley et al. |
| 5,928,284 A | 7/1999 | Mehdizadeh |
| 5,972,015 A | 10/1999 | Scribner et al. |
| 6,039,761 A | 3/2000 | Li et al. |
| 6,127,597 A | 10/2000 | Beyar et al. |
| 6,159,215 A | 12/2000 | Urbahns et al. |

(Continued)

FOREIGN PATENT DOCUMENTS

EP    0 260 044 A1    3/1988

(Continued)

OTHER PUBLICATIONS

U.S. Appl. No. 10/717,684, Trieu.

*Primary Examiner*—Anu Ramana

(57) ABSTRACT

Expandable devices include a body defining a hollow interior for receiving distal portion of a delivery instrument. The expandable devices are collapsed on the distal portion of the delivery instrument for delivery to the operative site within a vertebral body. Upon delivery of the collapsed expandable devices to the operative site, the distal portion of the delivery instrument is enlargeable to expand the expandable device in situ for implantation at the operative site.

20 Claims, 11 Drawing Sheets

U.S. PATENT DOCUMENTS

| | | | |
|---|---|---|---|
| 6,174,334 B1 | 1/2001 | Suddaby | |
| 6,183,517 B1 | 2/2001 | Suddaby | |
| 6,190,414 B1 | 2/2001 | Young et al. | |
| 6,248,110 B1 | 6/2001 | Reiley et al. | |
| 6,280,456 B1 | 8/2001 | Scribner et al. | |
| 6,306,177 B1 * | 10/2001 | Felt et al. | 623/23.6 |
| 6,332,894 B1 | 12/2001 | Stalcup et al. | |
| 6,402,785 B1 | 6/2002 | Zdeblick et al. | |
| 6,409,766 B1 | 6/2002 | Brett | |
| 6,419,704 B1 | 7/2002 | Ferree | |
| 6,419,705 B1 | 7/2002 | Erickson | |
| 6,423,083 B2 | 7/2002 | Reiley et al. | |
| 6,436,140 B1 | 8/2002 | Liu et al. | |
| 6,440,138 B1 | 8/2002 | Reiley et al. | |
| 6,443,989 B1 | 9/2002 | Jackson | |
| 6,454,807 B1 | 9/2002 | Jackson | |
| 6,491,724 B1 | 12/2002 | Ferree | |
| 6,527,799 B2 | 3/2003 | Shanley | |
| 6,582,467 B1 | 6/2003 | Teitelbaum et al. | |
| 6,632,235 B2 * | 10/2003 | Weikel et al. | 606/192 |
| 6,635,078 B1 * | 10/2003 | Zhong et al. | 623/1.11 |
| 6,676,665 B2 | 1/2004 | Foley et al. | |
| 2002/0026197 A1 | 2/2002 | Foley et al. | |
| 2002/0589947 | 5/2002 | Hochschuler et al. | |
| 2002/0183761 A1 | 12/2002 | Johnson et al. | |
| 2004/0097930 A1 | 5/2004 | Justis et al. | |

FOREIGN PATENT DOCUMENTS

| | | |
|---|---|---|
| WO | WO 00/35389 | 6/2000 |
| WO | WO 00/44319 | 8/2000 |
| WO | WO 01/19295 | 3/2001 |

* cited by examiner

SYSTEMS AND TECHNIQUES FOR INTRAVERTEBRAL SPINAL STABILIZATION WITH EXPANDABLE DEVICES

CROSS-REFERENCE TO RELATED APPLICATION

This application claims the benefit of the filing date of Provisional Application Ser. No. 60/428,061 filed on Nov. 21, 2002.

BACKGROUND

Spinal deformities and injuries can require intravertebral stabilization to restore fractured or deformed vertebral body to a desired condition. Intravertebral stabilization can include the intravertebral insertion and expansion of a balloon to compact cancellous bone tissue and create an intravertebral void. Cement material can then be placed in the intravertebral void. Other techniques include intravertebral placement and expansion of mechanical expansion instruments to reduce vertebral fractures, and the subsequent removal of the instrument followed by placement of bone cement. In either case, post-reduction support of the vertebra can be provided by bone cement placed in a void formed in the vertebral body.

Intravertebral reduction with balloons and instruments can result in loss of support for the reduced vertebra when the balloon or instrument is removed to accommodate placement of material in the void created. Further, expansion or enlargement of balloons and expandable instruments in the compressible cancellous bone material can provide inconsistent results since the bone material can influence the direction and degree of expansion. Vertebroplasty techniques which include the injection of bone filler into the vertebral body can require the bone filler to be injected under high pressures with low viscosity, increasing the difficulty in controlling and targeting the filler material into the desired areas within the vertebral body.

There remains a need for additional improvements in instruments and techniques for intravertebral spinal stabilization which address these deficiencies, among others.

SUMMARY

In one aspect, a method for intravertebral reduction, comprises: accessing a vertebral body; forming an access passage into the vertebral body; delivering an expandable device through the passage into the vertebral body in an unexpanded condition; expanding the expandable device in the vertebral body with an expandable element; removing the expandable element; and placing bone filler material within the expanded expandable device.

In another aspect, a method for intravertebral reduction, comprises: accessing a vertebral body; forming an access passage into the vertebral body; delivering an expandable device through the passage into the vertebral body in an unexpanded condition; expanding the expandable device with an expandable element in the expandable device to restore a vertebral body height; removing the expandable element; and maintaining the restored vertebral height device with the expanded expandable device.

In a further aspect, a system for intravertebral reduction includes a delivery instrument with an expandable element along a distal portion thereof. The system further includes an expandable device including a cavity. The expandable device is removably mountable to the expandable element with the expandable element in the cavity and each of the expandable device and the expandable element in an unexpanded condition. The expandable device is deliverable to an intravertebral space in the unexpanded condition and thereafter expandable with expansion of the expandable element to compress cancellous bone in the intravertebral space.

In another aspect, a system for intravertebral reduction includes a delivery instrument with a non-rigid expandable element along a distal portion thereof. The system further includes an expandable device with a cavity between substantially rigid first and second portions. The expandable device is structured for positioning in an intravertebral space. When expandable element is positioned in the cavity it is expandable to move the first and second portions away from one another and compress cancellous bone in the intravertebral space.

These and other aspects are also presented in the following description.

DESCRIPTION OF THE ILLUSTRATED EMBODIMENTS

Figure 1:
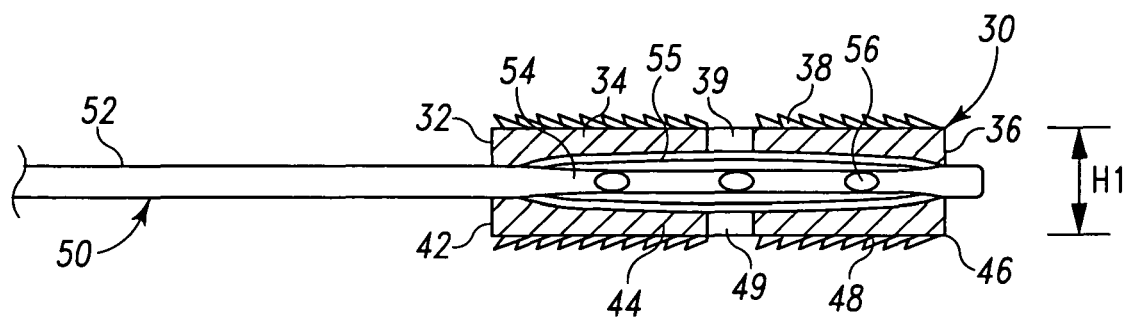
FIG. 1 is a sectional view of a collapsed expandable device and delivery instrument.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated herein are contemplated as would normally occur to one skilled in the art to which the invention relates.

There are provided systems and methods for positioning and deploying expandable devices in bony structures of a spinal column segment. Such systems can include instruments for delivering the expandable devices to the operative site and expanding the expandable devices in situ. When positioned for intravertebral reduction, the expandable devices provide a substantially rigid interface with the cancellous bone to direction compression forces thereto in a controlled and repeatable manner when the expandable devices are expanded. Such expansion can compress cancellous bone, provide size and/or shape restoration to bony structures, and provide immediate and long-term support of the reduced vertebra.

According to one embodiment, the delivery instrument includes a balloon catheter-type instrument having an enlargeable member adjacent a distal portion of the delivery instrument. A collapsed or unexpanded expandable device is positioned about the expandable member and secured thereto for delivery to the operative site in the unexpanded configuration. The delivery instrument can be employed in minimally invasive surgical procedures to deliver the collapsed or unexpanded expandable device to the operative site. Upon positioning the expandable device at the operative site, the distal portion of the delivery instrument is expandable to deploy and expand the expandable device at the operative site. Such deployment and expansion of the expandable device can, for example, compress cancellous bone when deployed in an intravertebral space. The expandable device can provide at least temporary support of the vertebra. Bone filler material can be positioned in a void formed at least partially by the expanded expandable device.

Delivery and expansion of the expandable device in the intravertebral space provides mechanical reduction of vertebral fractures or deformities, and post-operative mechanical support for the fractured or deformed vertebral body. Reduction of the vertebral fracture can be targeted by positioning the expandable device in a location where at least one portion of the expandable device can provide a substantially rigid interface with the cancellous bone between the device and the fracture as the device is expanded. The expandable devices can provide at least temporary maintenance of the reduction achieved through expansion while bone filler material is positioned within the expandable device. The expandable device can be provided with one or more openings in its first and second portions, and one or more openings at its proximal and distal ends, to facilitate bony incorporation of the expandable device in the vertebral body.

The systems and methods can be employed in minimally invasive surgical approaches to the spine. Such approaches include anterior, posterior, transforaminal, lateral, oblique, transpedicular, extrapedicular, and other approaches to a vertebral body. The approaches can be uni-portal or multi-portal in nature. The approaches can be to any portion of the spinal column segment, including the sacral, lumbar, thoracic, and cervical regions. The systems and methods can be employed with any viewing system to assist in monitoring placement of the expandable devices intravertebrally. Examples of suitable viewing systems include fluoroscopic, endoscopic, microscopic, CT scan, X-ray, and naked eye visualization systems.

Figure 2:
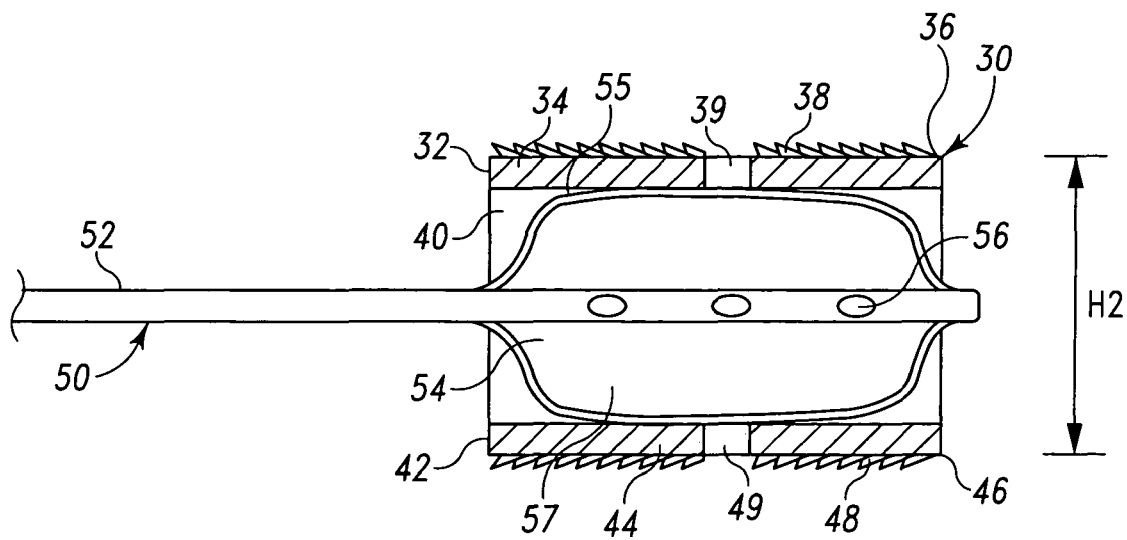
FIG. 2 is the expandable device and delivery instrument of FIG. 1 in an expanded condition.

Referring now to FIGS. 1 and 2, there is shown a first embodiment of an expandable device 30. In this embodiment, expandable device 30 includes an elongated body that includes a first portion 34 positionable toward one endplate of a vertebra and a second portion 44 positionable toward the opposite endplate of the vertebra. First portion 34 extends between a distal leading insertion end 36 and a proximal trailing end 32. Second portion 44 extends between a distal leading insertion end 46 and a proximal trailing end 42. A cavity 40 is defined between first portion 34 and second portion 44. Cavity 40 can extend between and open at distal end 36 and trailing end 32.

First portion 34 can be provided with a number of engagement members 38, and second portion 44 can also be provided with a number of engagement members 48. Engagement members 38, 48 can be in the form of teeth, spikes, ridges, threads, barbs, knurlings, protrusions, fins, and combinations thereof, for example. It is further contemplated that the outer surfaces can be smooth, or auxiliary fixation or engagement members can be provided. First and second portions 34, 44 can further include one or more openings 39, 49, respectively, to facilitate bone ingrowth.

First portion 34 and second portion 44 are movable away from one another from an unexpanded configuration, as shown in FIG. 1, to an expanded configuration, as shown in FIG. 2. In the unexpanded configuration, expandable device 30 has a height H1 between first portion 34 and second portion 44 as shown in FIG. 1. In the expanded configuration, expandable device 30 has a height H2 between first portion 34 and second portion 44. It is contemplated that height H1 will allow expandable device 30 to be inserted, for example, in a passage drilled into a vertebral body. Height H2 can correspond to a separation distance between first and second portions 34, 44 require to reduce a vertebral fracture or deformity, or provide a desired vertebral body height, for example.

A delivery instrument 50 can be provided to move expandable device 30 from its unexpanded configuration to its expanded configuration. Delivery instrument 50 includes a proximal shaft 52 and a distal portion 54 including an expandable element 55. In the illustrated embodiment, expandable element 55 is an inflatable balloon-like structure having a collapsed configuration, as shown in FIG. 1, and an enlarged, inflated configuration, as shown in FIG. 2. Shaft 52 can be provided with a lumen through which fluid or material can be supplied through openings 56 to internal volume 57 of expandable element 55 to enlarge or inflate expandable element 55. Expandable element 55 is positionable in cavity 40 of expandable device 30 with each of the expandable element 55 and expandable device 30 in its unexpanded or collapsed configuration.

After delivery of expandable device 30 to the operative site, expandable element 55 can be inflated to provide an enlarged configuration for expandable element 55 and thus separate first and second portions 34, 44 of expandable device 30 as shown in FIG. 2. As expandable device 30 is expanded, first portion 34 and second portion 44 move away from one another and the volume of cavity 40 is increased. This expansion can compress cancellous bone and reduce vertebral fractures and/or restore a vertebral body height when device 30 is positioned intravertebrally.

One example of a suitable delivery instrument 50 includes a high-pressure balloon catheter. Shaft 52 can be rigid, semi-rigid, or flexible. Shaft 52 can be fabricated from metals, polymers, or combinations thereof. Shaft 52 can be provided with at least one lumen to allow inflation or enlargement of expandable element 55 with a biocompatible fluid, such as air or saline, for example. Other embodiments contemplate that shaft 52 includes multiple lumens to, for example, deliver bone graft, bone growth material or other suitable bone filler material into the expanded cavity 40 of an expanded device 30. It is contemplated that expandable element 55 is collapsed prior to or simultaneously with placement of the bone filler material.

In the illustrated embodiment, distal portion 54 includes a single expandable element, although multiple expandable elements are also contemplated to provide distal portion 54 with alternate enlargement characteristics. For example, distal portion 54 could include a distal expandable element and a proximal expandable element having differing heights to provide angulation between the expanded first and second portions 34, 44 of expandable device 30. In another example, distal portion 54 can include an upper expandable element and a lower expandable element which can be selectively expanded move the adjacent one of first and second portions 34, 44 while the other of the first and second portions remains stationary. In a further example, expandable element 55 expands uni-directionally to move the adjacent one of the first and second portions 34, 44 in the direction of expansion to provide intra-vertebral reduction in a targeted location.

In another embodiment, it is contemplated that distal portion 54 can be severed from shaft 52 after expansion, and post-operatively maintain expandable device 30 in an expanded condition. Accordingly, expandable element 55 can be inflated with bone growth material or other suitable bone filler material to facilitate bone growth in an intravertebral space through the expanded device 30. Expandable element 55 can be fabricated from porous material, resorbable material, or other suitable material to allow bone growth through the cavity of the expanded device.

Expandable element 55 can include a size and shape that matches the size and shape of cavity 40 in its expanded configuration. In the expanded configuration, expandable element 55 can apply a uniform expansion force along the inner wall surfaces of first portion 34 between leading end 36 and trailing end 32. If configured for bidirectional expansion as shown in FIG. 2, expandable element 55 can apply a uniform expansion force along second portion 44 between leading end 46 and trailing end 42. Expandable element 55 can be provided with any suitable overall shape including conical, frusto-conical, spherical, cubic, spherical, polygonal, ovoid, long conical, long spherical, rectangular, tapered, stepped, dog-bone shape, offset shapes and combinations thereof.

Expandable element 55 can be made from any suitable material capable of withstanding the pressure supplied to enlarge or inflate expandable element 55 in situ. Examples include various polymeric materials, including polyethylene, terephthalates, polyolefins, polyurethanes, nylon, polyvinyl chloride, silicone or other suitable material. The material comprising expandable element 55 can be reinforced with woven or non-woven textile materials. Examples of suitable reinforcement materials include those that are polymeric and metallic in nature.

Figure 3:
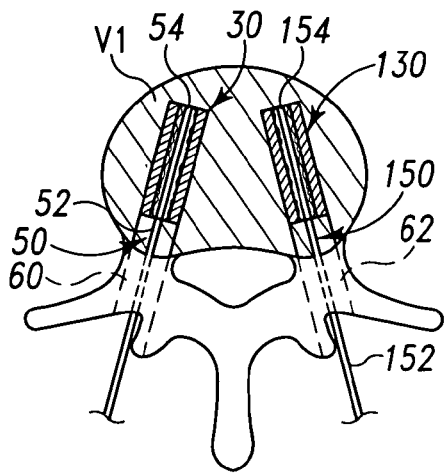
FIGS. 3 and 4 are a plan view and an elevation view in partial section, respectively, of a spinal column segment having a pair of expandable devices and delivery instruments positioned in an intravertebral space in an unexpanded condition.
Figure 4:
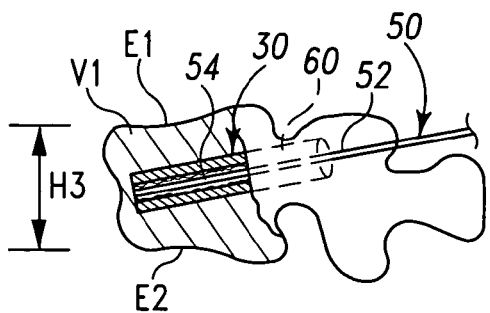

Referring now to FIGS. 3 through 8, there is shown an example of a surgical technique employing the expandable devices and delivery instruments for intravertebral repair and/or restoration of a collapsed, pressure fractured or otherwise deformed vertebral body. In FIGS. 3 and 4, there is shown a spinal column segment including a vertebra V1 having an upper endplate E1 and a lower endplate E2. Vertebra V1 has a reduced anterior height configuration H3 as a result of a compression fracture, collapse or other deformity or condition of one or each of the endplates E1, E2 and the vertebral body extending therebetween.

Posterior access passages 60, 62 are formed through the pedicles of vertebra V1 to access the interior of vertebral body V1. Passages 60, 62 can be formed by drilling or cutting the bony material of the pedicles to access the interior cancellous bony portion of vertebra V1. Other locations for passages 60, 62 are also contemplated, including extrapedicular approaches to vertebra V1 from a posterior-lateral approach, and also lateral, anterior-lateral, and anterior approaches. It is further contemplated that a single passage can be formed or more than two passages can be formed for any of these approaches.

In the illustrated embodiment, a second expandable device 130 and a second delivery instrument 150 are provided for placement through the second passage 62. Expandable device 130 and delivery instrument 150 can be identical to expandable device 30 and delivery instrument 50 discussed above, although such is not required. It is further contemplated that the same delivery instrument 50 can be employed to position the second expandable device 130 after placement and expansion of the first expandable device 30.

Figure 5:
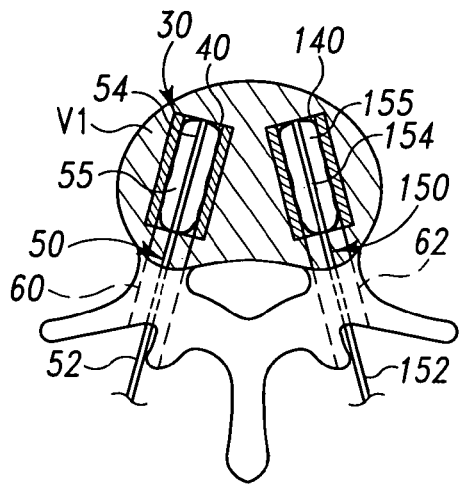
FIGS. 5 and 6 are a plan view and an elevation view in partial section, respectively, with the expandable devices and delivery instruments of FIGS. 3 and 4 in an expanded condition in the intravertebral space.
Figure 6:
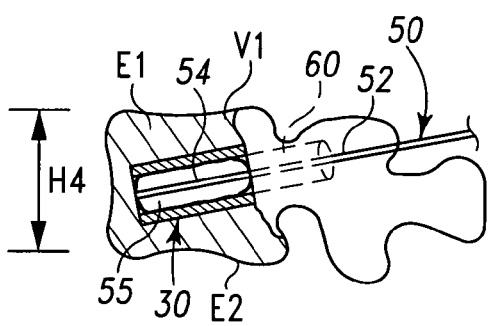

Unexpanded expandable devices 30, 130 are attached to respective ones of the collapsed distal portions 54, 154 of delivery instruments 50, 150 for delivery to the operative site. It is contemplated that the attachment can be provided by adhesive, frictional or form-fitting interengagement, or mechanical fasteners, for example. Expandable devices 30, 130 are then placed through the respective passages 60, 62 and into the intravertebral space of vertebra V1. A radio-contrast fluid, saline solution, compressed air, or other suitable fluid can be delivered to distal portions 54, 154 through shafts 52, 152 by a syringe or pump operable. The fluid provides sufficient pressure for expansion of expandable elements 55, 155 and thus expand expandable devices 30, 130 as shown in FIGS. 5 and 6. As the pressure and volume of the respective expandable elements 55, 155 increase, the first and second portions of expandable devices 30, 130 are gradually separated and provide an interface that compresses the surrounding cancellous bone to, for example, restore to height H4 a collapsed or fractured vertebra V1.

Figure 7:
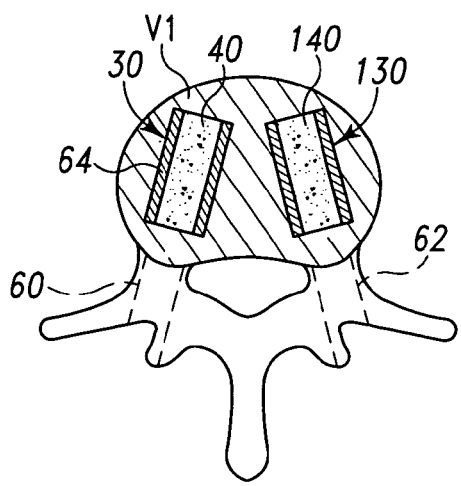
FIGS. 7 and 8 are a plan view and an elevation view in partial section, respectively, with expanded expandable devices of FIGS. 5 and 6 in the intravertebral space and the delivery instruments removed.
Figure 8:
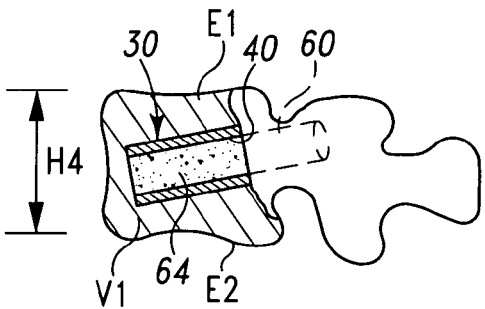

Expandable elements 55, 155 are then deflated or collapsed, and distal portions 54, 154 removed from their respective expanded expandable devices 30, 130 as shown in FIGS. 7 and 8. Expandable devices 30, 130 can be adapted to maintain the desired vertebral height H4 after removal of expandable elements 55, 155 without internal pressure or support being applied to the vertebral body or the expanded devices 30, 130. The expanded devices 30, 130 provide a cavity for placement of bone filler material under low pressures and high viscosity, reducing the time for curing and stabilization to be supplemented with the bone filler material.

Bone filler material 64 is then placed in cavity 40 of the expanded expandable device 30, and can also be placed in cavity 140 of expandable device 130. Passages 60, 62 can also be filled with bone filler material 64. Bone filler material 64 can be deposited, packed, or injected into the cavities 40, 140 of expanded expandable devices 30, 130 and/or into the intravertebral space adjacent thereto to provide long term support and stability of vertebra V1 with bone formation.

Any suitable osteogenic material or composition is contemplated for the filler material, including autograft, allograft, xenograft, demineralized bone, and synthetic and natural bone graft substitutes, such as bioceramics and polymers, and osteoinductive factors. The terms osteogenic material or osteogenic composition used herein broadly include any material that promotes bone growth or healing including autograft, allograft, xenograft, bone graft substitutes and natural, synthetic and recombinant proteins, hormones and the like.

Autograft can be harvested from locations such as the iliac crest using drills, gouges, curettes, and trephines and other tools and methods which are well known to surgeons in this field. Preferably, autograft is harvested from the iliac crest with a minimally invasive donor surgery. The osteogenic material may also include bone reamed away by the surgeon while preparing the endplates.

Natural and synthetic graft substitutes which replace the structure or function of bone are also contemplated for the osteogenic composition. Any such graft substitute is contemplated, including for example, demineralized bone matrix, demineralized bone matrix with bone chips, PMMA and other injectable synthetic bone cements, mineral compositions, and bioceramics. A vast array of bioceramic materials, including BIOGLASS®, hydroxyapatite, and calcium phosphate compositions known in the art which can be used to advantage for this purpose. Preferred calcium compositions include bioactive glasses, tricalcium phosphates, and hydroxyapatites. In one embodiment, the graft substitute is a biphasic calcium phosphate ceramic including tricalcium phosphate and hydroxyapatite.

In some embodiments, the osteogenic compositions used can comprise a therapeutically effective amount to stimulate or induce bone growth of a bone inductive or growth factor or protein in a pharmaceutically acceptable carrier. Osteoinductive factors that are recombinant human bone morphogenetic proteins (rhBMPs) are contemplated because they are readily available and do not contribute to the spread of infectious diseases. The bone morphogenetic protein can be a rhBMP-2, rhBMP-4 or heterodimers thereof. However, any bone morphogenetic protein is contemplated including bone morphogenetic proteins designated as BMP-1 through BPM-13.

The choice of carrier material for the osteogenic composition is based on biocompatibility, biodegradability, mechanical properties, and interface properties as well as the structure of the expandable device. Potential carriers include calcium sulphates, polylactic acids, polyanhydrides, collagen, calcium phosphates, polymeric acrylic esters, and demineralized bone. The carrier may be any suitable carrier capable of delivering the proteins. The carrier can be capable of being eventually resorbed into the body, such as an absorbable collagen sponge marketed by Integra LifeSciences Corporation under the trade name Helistat® Absorbable Collagen Hemostatic Agent. Another carrier is a biphasic calcium phosphate ceramic. Ceramic blocks are commercially available from Sofamor Danek Group, B.P. 4-62180 Rang-du-Fliers, France, and Bioland, 132 Rou d Espangne, 31100 Toulouse, France. The osteoinductive factor is introduced into the carrier in any suitable manner. For example, the carrier may be soaked in a solution containing the factor. One preferred embodiment contemplates use of OSTEOFIL® allograph paste sold by Regeneration Technologies, Inc. The allograph paste can be supplemented with a local autograft obtained from the cutting operation.

Figure 9:
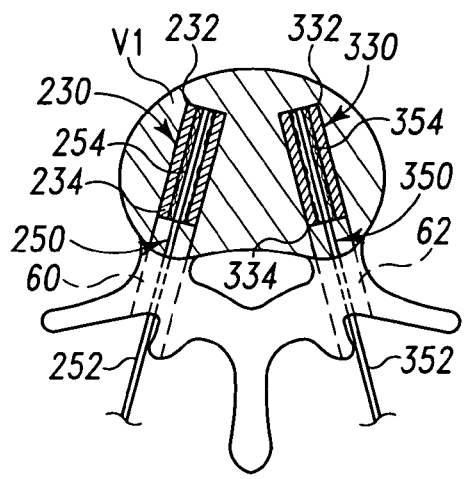
FIGS. 9 and 10 are a plan view and an elevation view in partial section, respectively, of a spinal column segment and another embodiment pair of expandable devices and delivery instruments positioned in an intravertebral space in an unexpanded condition.
Figure 10:
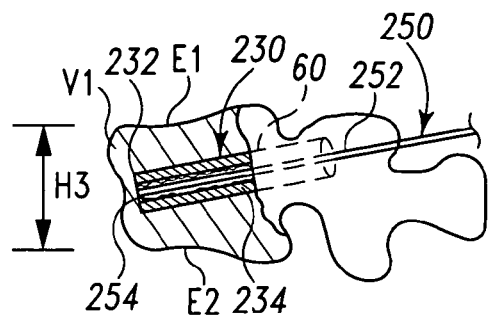

Referring now to FIGS. 9 through 14, there is shown an example of a surgical technique employing another embodiment expandable device and delivery instrument intravertebrally for repair and/or restoration of a collapsed or pressure fractured vertebral body. In FIGS. 9 and 10, there is shown a spinal column segment including vertebra V1 having upper endplate E1 and lower endplate E2. Vertebra V1 includes a reduced anterior height configuration H3 as a result of a compression fracture, collapse or other deformity or condition of one or each of the endplates E1, E2 and the vertebral body extending therebetween.

In FIGS. 9-14, expandable devices 230, 330 are provided that are similar to expandable device 30 discussed above, but include a tapered configuration such that the distal ends 232, 332 can expand or separate a greater distance than proximal ends 234, 334. Accordingly, when positioned in the vertebral body V1 from a posterior approach, distal ends 232, 332 are positionable adjacent the anterior portion of vertebra V1 requiring restoration. Other tapered configurations are also contemplated such as, for example, proximal ends that can expand or separate a greater distance than the distal ends. Such an alternate device could be employed in a vertebra with an anterior fracture in an anterior approach to the vertebra.

Delivery instruments 250, 350 can be configured like delivery instrument 50 discussed above, but include one or more expandable elements 255, 355 along distal portions 254, 354 that include a shape adapted to expand the internal cavities 236, 336 of expandable devices 230, 330. Expandable elements 255, 355 can be tapered, stepped or otherwise configured to effect greater expansion at distal ends 232, 332 than at proximal ends 234, 334.

Figure 11:
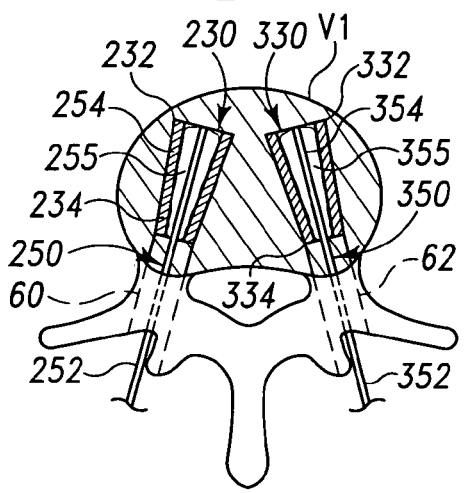
FIGS. 11 and 12 are a plan view and an elevation view in partial section, respectively, with expandable devices and delivery instruments of FIGS. 9 and 10 in an expanded condition in the intravertebral space.
Figure 12:
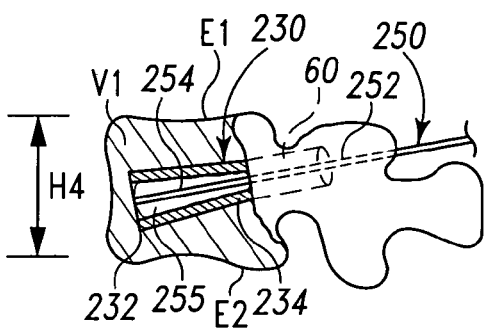

Unexpanded expandable devices 230, 330 are attached to collapsed expandable elements 254, 354 of delivery instruments 250, 350 for delivery of expandable devices 230, 330 to the operative site. Expandable devices 230, 330 are then placed through the passages 60, 62 and into the intravertebral space of vertebra V1. A radio-contrast fluid, saline solution, compressed air, or other suitable fluid can be delivered through shafts 252, 352 to expandable elements 255, 355 through a syringe or pump operable to provide sufficient pressure to expand expandable devices 230, 330 as shown in FIGS. 11 and 12. As the pressure and volume of the respective expandable elements 255, 355 increase, expandable devices 230, 330 are gradually expanded and compress the surrounding cancellous bone to restore the collapsed vertebra V1 from height H3 to a desired vertebral body height H4 between endplates E1 and E2.

Figure 13:
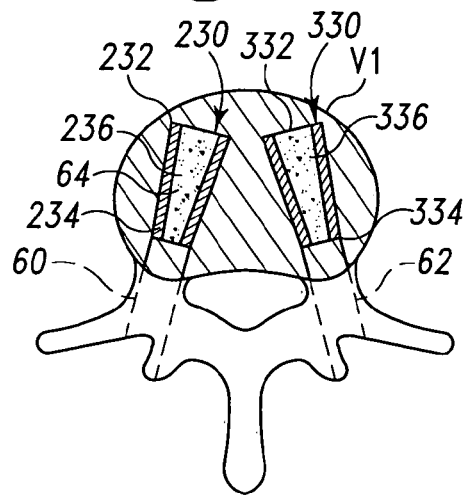
FIGS. 13 and 14 are a plan view and an elevation view in partial section, respectively, with the expandable devices of FIGS. 11 and 12 expanded in the intravertebral space and the delivery instruments removed.
Figure 14:
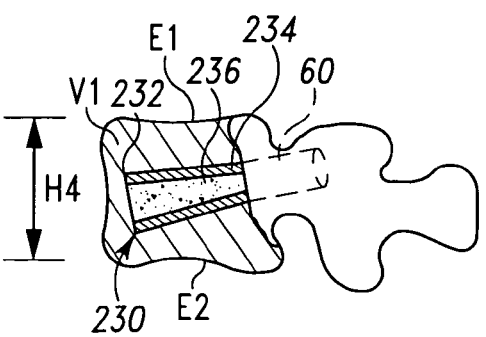

Expandable elements 255, 355 are then deflated or collapsed and removed from their respective expanded expandable devices 230, 330, as shown in FIGS. 13 and 14. Bone filler material 64 can be deposited, packed, or injected into the cavities 236, 336 of the expanded devices 230, 330 to provide long term support and stability of vertebra V1 during bone formation.

Figure 15:
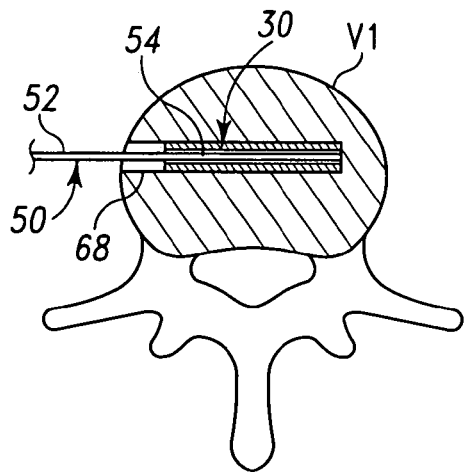
FIGS. 15 and 16 are a plan view in partial section and an elevation view, respectively, of a spinal column segment having an expandable device and delivery instrument positioned in an intravertebral space in an unexpanded condition.
Figure 16:
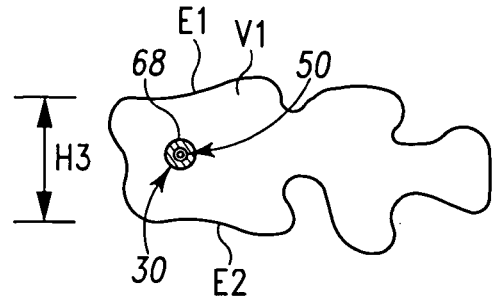
Figure 17:
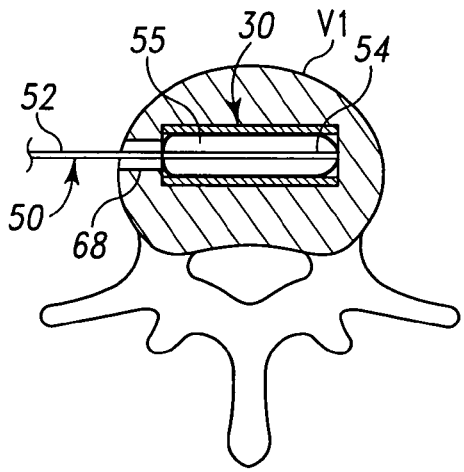
FIGS. 17 and 18 are a plan view in partial section and an elevation view, respectively, with the expandable device and delivery instrument of FIGS. 15 and 16 in an expanded condition in the intravertebral space.
Figure 18:
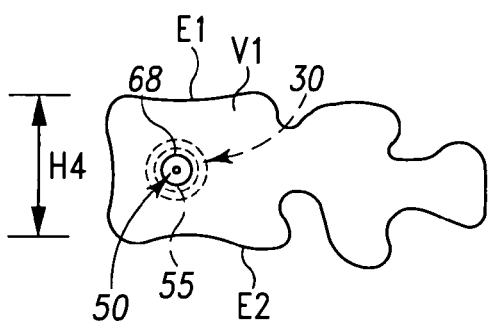
Figure 19:
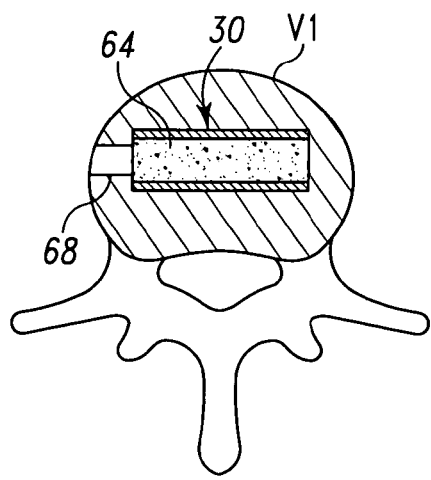
FIGS. 19 and 20 are a plan view in partial section and an elevation view, respectively, with the expanded expandable device of FIGS. 17 and 18 in the intravertebral space and the delivery instrument removed.
Figure 20:
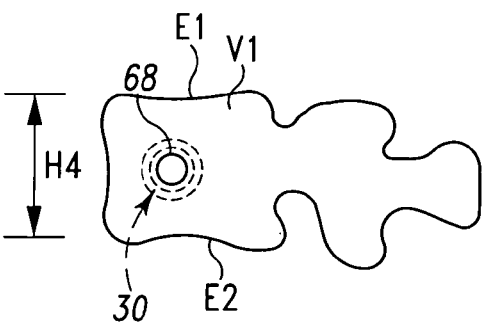

Intravertebral reduction can also be conducted from other approaches to the vertebral body, such as a lateral approach shown in FIGS. 15-20. A lateral access passage 68 is formed in vertebra V1 to provide assess to the cancellous bony material in the interior of the vertebral body. Expandable device 30 is positioned on distal portion 54 of delivery instrument 50, and delivery instrument 50 is positioned to deliver expandable device 50 into vertebra V1 through lateral access passage 68, as shown in FIGS. 15 and 16. Expandable element 55 is expanded to expand expandable device 30 in vertebra V1, as shown in FIGS. 17 and 18. The expanded expandable device 30 compresses the cancellous bony tissue and restored vertebra V1 to a restored height H4 adjacent at the anterior portion of vertebra V1. In FIGS. 19 and 20, delivery instrument 50 is removed from access passage 68, and bone filler 64 is positioned in the cavity of expandable device 30.

In the embodiment of FIGS. 15-20, it is also contemplated that expandable device 30 can be configured to separate a greater distance along the side thereof positioned adjacent the vertebral fracture.

Figure 21:
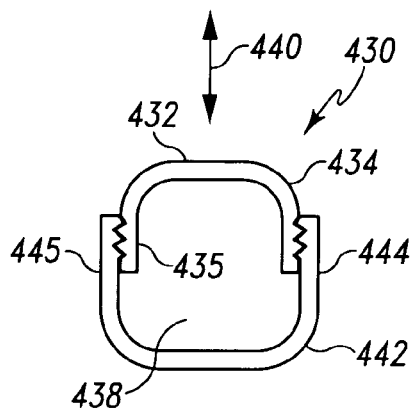
FIG. 21 is an end view of another embodiment expandable device.

The expandable devices contemplated herein can be provided in various forms. For example, as shown in FIG. 21, the first and second portions of the expandable device could be adjustably connected along overlapping sidewalls of the first and second portions. Expandable device 430 includes a first portion 432 and a second portion 442 similar to expandable device 30 discussed above. First portion 432 includes opposite sidewalls 434, 435, and second portion 442 includes opposite sidewalls 444, 445. First portion 432 and second portion 442 define a cavity 438 therebetween into which expandable element 55 of delivery instrument 50 can be positioned.

The adjacent sidewalls 434, 444 include a number of interdigitating teeth that engage one another, and the adjacent sidewalls 435, 445 include a number of interdigitating teeth that engage one another. The interdigitating teeth allow first and second portions 432, 442 to be uni-directionally moved away from one another upon expansion of expandable element 55 in cavity 438 as indicated by arrows 440. The interdigitating teeth can include a ratcheted configuration that resists or prevents movement of first and second portions 432, 442 toward one another after expansion. Expandable device 430 maintains support of the reduced vertebra immediately after reduction, even after removal of expandable element 55 from cavity 438. The interdigitating teeth further define a number of expanded or separated positions between first and second portions 432, 442 that provide various reduction heights that can be effected with a single expandable device 430.

In another example, the expandable devices could be made from a shape memory material or ductile that is unexpanded or collapsed for positioning on the delivery instrument prior to insertion. Upon insertion to the surgical location, the device is radially expandable with inflation or enlargement of the delivery instrument to assume an expanded configuration. Expansion of the expandable device can be accomplished with temperature changes, chemical changes, or force induced changes with inflation or enlargement of the enlargeable member 55 of delivery instrument 50.

Figure 22:
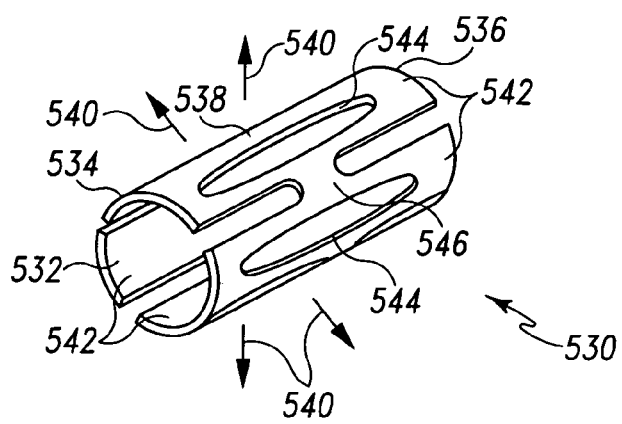
FIG. 22 is a perspective view of another embodiment expandable device in an unexpanded configuration.

For example, in FIG. 22 there is shown expandable device 530 including a body 538 defining an interior cavity 532 extending between a proximal end 534 and a distal end 536. Body 538 includes a number of portions 542 therearound that each define an elongated flex opening 544. Segments 542 are interconnected by hinges 546. Body 538 is made of sufficiently ductile or formable material such that upon exertion of a radial expansion force, indicated by arrows 540, flex openings 544 can enlarge and hinges 546 can stretch to allow segments 542 to move away from one another, enlarging interior cavity 532.

In a further example, the expandable devices can include a first mechanical configuration that allows a collapsed condition for insertion of the device with the delivery instrument. After insertion, the device can be mechanically adjusted upon inflation or enlargement of the distal portion of the delivery instrument to assume an expanded condition at the operative site. Examples of such expandable devices include those made from a wire mesh material, and devices with first and second portion connected by mechanical linkages, as shown in FIGS. 23-25.

Figure 23:
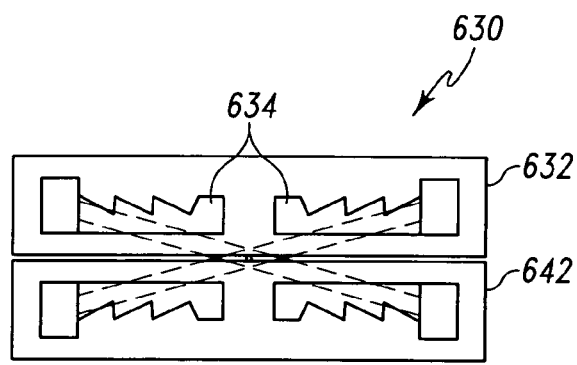
FIG. 23 is an elevation view of another embodiment expandable device in an unexpanded configuration.
Figure 25:
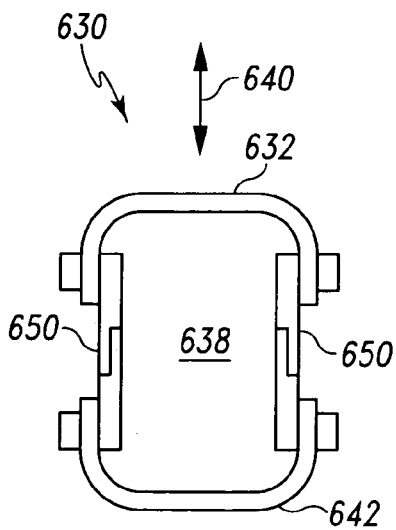
FIG. 25 is an end view of the expanded expandable device of FIG. 24.
Figure 24:
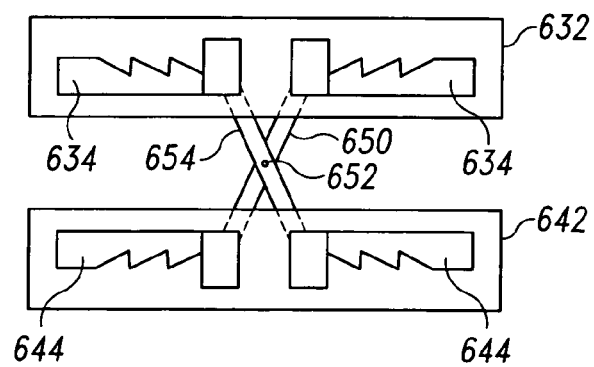
FIG. 24 is an elevation view of the expandable device of FIG. 23 in an expanded configuration.

In FIGS. 23-25 device 630 includes a first portion 632 and a second portion 642. Linkages 650 movably couple first and second portions 632, 642 to one another. Linkages 650 include first and second members 652, 654 pivotally coupled to one another. Members 652, 654 each include a first end positioned in respective ones of the receptacles 634 of first portion 632, and opposite second ends positioned in respective ones of the receptacles 644 of second portion 642. The ends of the members 650, 652 can include a configuration that interdigitates with a ratchet surface formed along the respective receptacles 634, 644. In the unexpanded configuration shown in FIG. 23, the ends of members 652, 654 are positioned at the outer ends of the respective receptacles 634, 644.

As first and second portions 632, 642 are uni-directionally moved away from one another with expandable element 55 in cavity 638, as indicated by arrows 640, the ends of members 650, 652 move longitudinally toward one another along the receptacles 634, 644 of each of the respective first and second portions 632, 642, as shown in FIG. 24. The rigid members 652, 654 move first and second portions 632, 642 away from one another, and engage the ratchet surfaces along receptacles 634, 644 to maintain the expanded or separated position between first and second portions 632, 642, as shown in FIGS. 24 and 25.

Figure 26A:
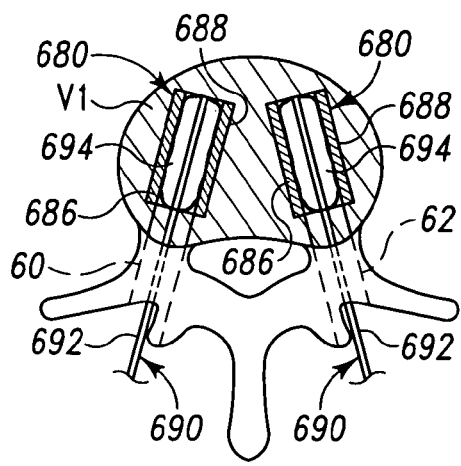
FIGS. 26A and 26B are a plan view and an elevation view in partial section, respectively, of collapsed expandable devices and delivery instruments according to another embodiment positioned in an intravertebral space of a vertebra.
Figure 26B:
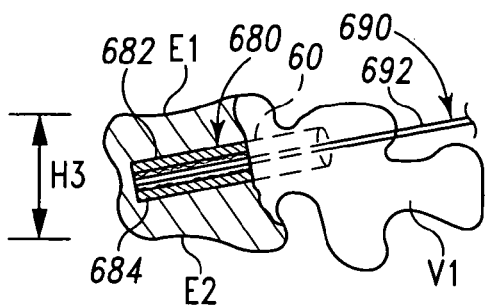

FIGS. 26A and 26B are a plan view and an elevation view in partial section, respectively, of another embodiment pair of collapsed expandable devices 680 and associated delivery instruments 690 positioned in an intravertebral space of vertebra V1. The collapsed or unexpanded expandable devices 680 are secured around the respective unexpanded expandable element 694 at a distal end of delivery instrument 690 for delivery to the intravertebral space. In the illustrated embodiment, vertebra V1 is accessed from a posterior approach through the pedicles, although other approaches are also contemplated. Expandable devices 680 each include a width between opposite sides 686, 688.

Figure 27A:
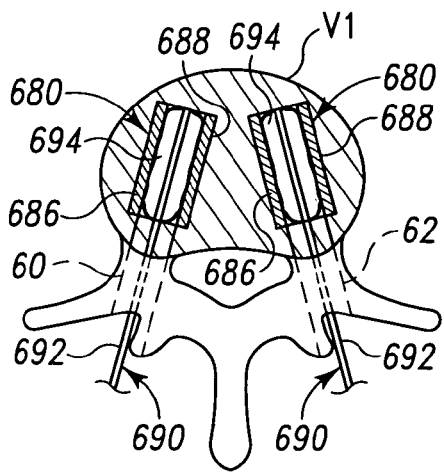
FIGS. 27A and 27B are a plan view and an elevation view in partial section, respectively, with expanded expandable devices and delivery instruments positioned in the intravertebral space and the vertebra reduced.
Figure 27B:
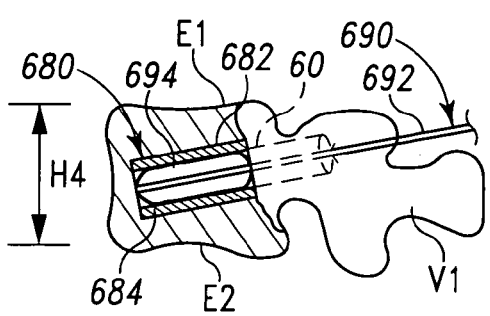

FIGS. 27A and 27B are a plan view and an elevation view in partial section, respectively, with expandable devices 680 expanded with a fluid delivered through shafts 692 of delivery instruments 690. In the expanded condition, lower and upper surfaces 682, 684 of expandable device 680 compress the surrounding cancellous bone to reduce vertebra V1 from height H3 to a greater restored height H4. The widths between opposite sides 686, 688 of expandable devices 680 remain substantially constant during and after expansion. Accordingly, expandable devices 680 are vertically expandable to increase their height while their widths remain constant, such as shown with expandable devices 430 and 630 discussed above.

Figure 28A:
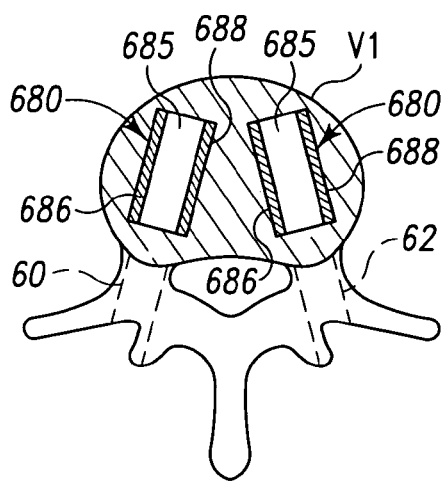
FIGS. 28A and 28B are a plan view and an elevation view in partial section, respectively, with expanded expandable devices in the intravertebral space of the reduced vertebra and the delivery instruments removed.
Figure 28B:
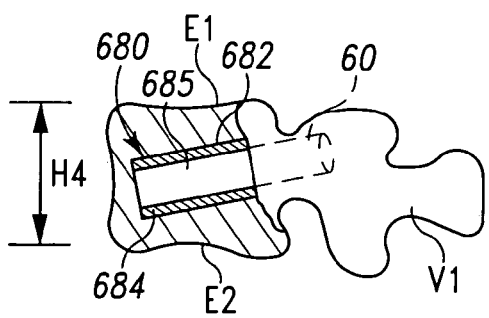

FIGS. 28A and 28B are a plan view and an elevation view in partial section, respectively, with the expanded expandable devices 680 in the restored vertebra V1 of the spinal column segment and the delivery instruments 690 removed from cavities 685 of expandable devices 680. Filler material for bone growth can be placed in cavities 685 and in approaches 60, 62 as discussed above.

Figure 29A:
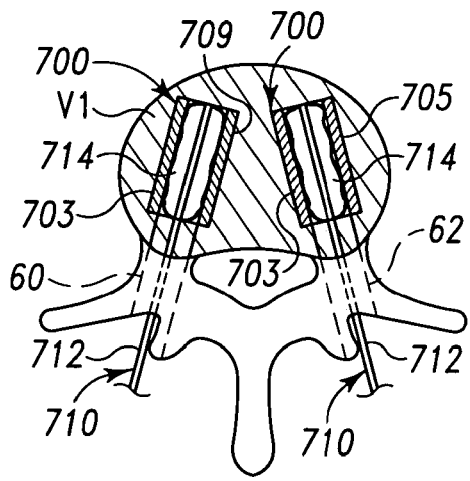
FIGS. 29A and 29B are a plan view and an elevation view in partial section, respectively, of collapsed expandable devices and delivery instruments according to another embodiment positioned in an intravertebral space of a vertebra.
Figure 29B:
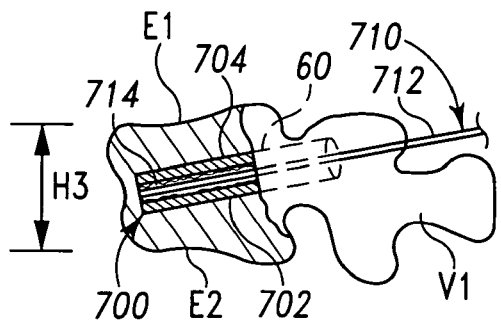

FIGS. 29A and 29B are a plan view and an elevation view in partial section, respectively, of another embodiment pair of collapsed expandable devices 700 and associated delivery instruments 710 positioned in vertebra V1. The collapsed or unexpanded expandable devices 700 are secured around the respective unexpanded expandable element 714 at a distal end of delivery instrument 710 for delivery to the intravertebral space. In the illustrated embodiment, the intravertebral space is accessed from a posterior approach through the pedicles, although other approaches are also contemplated. Expandable devices 700 include a width between opposite sides 703, 705.

Figure 30A:
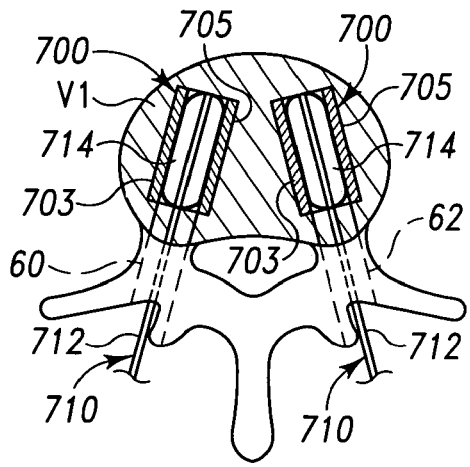
FIGS. 30A and 30B are a plan view and an elevation view in partial section, respectively, with expanded expandable devices and delivery instruments in the intraverebral space of and the vertebra reduced.
Figure 30B:
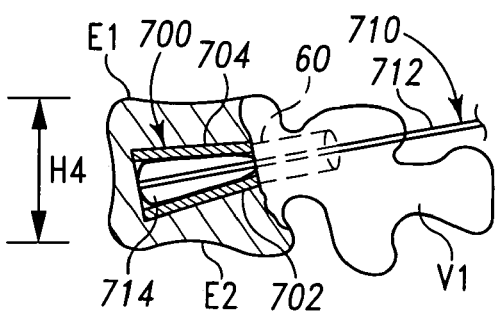

FIGS. 30A and 30B are a plan view and an elevation view in partial section, respectively, with expandable devices 700 expanded with a fluid delivered through shafts 712 of delivery instruments 710. In the expanded condition, lower and upper surfaces 702, 704 of expandable devices 700 compress the surrounding cancellous bone and separate the opposite vertebral endplates to reduce vertebra V1 from height H3 to provide a restored height H4. The widths between opposite sides 703, 705 of expandable devices 700 remain substantially constant during and after expansion. Accordingly, expandable devices 700 are vertically expandable to increase their height while their widths remain constant.

Expandable devices 700 are tapered along the length thereof between an anterior end and a posterior end. In the illustrated embodiment, the posterior end includes a first height 708, and the anterior end includes a second height 709 which is greater than first height 708. This tapered height provides a greater reduction of vertebra V1 adjacent the anterior portion thereof, which can be targeted to the region of greatest compression such as provided with an anterior vertebral fracture.

Figure 31A:
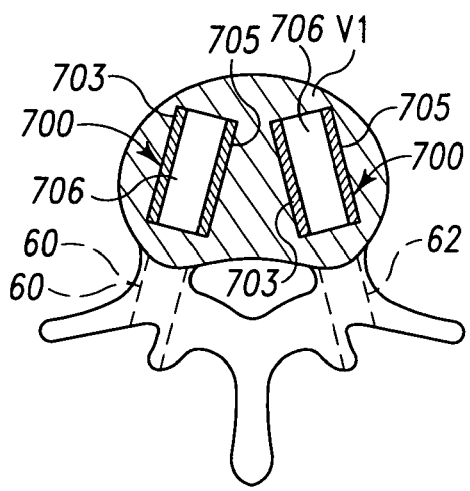
FIGS. 31A and 31B are a plan view and an elevation view in partial section, respectively, with expanded expandable devices in the intravertebral space of the reduced vertebra and the delivery instruments removed.
Figure 31B:
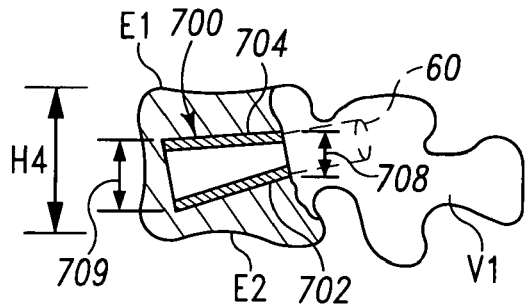

FIGS. 31A and 31B are a plan view and an elevation view in partial section, respectively, with the expanded expandable devices 700 in the reduced vertebra V1 of the spinal column segment and the delivery instruments 710 removed from cavities 706 of expandable devices 700. Filler material for bone growth can be placed in cavities 706 and in approaches 60, 62 as discussed above.

Figure 32A:
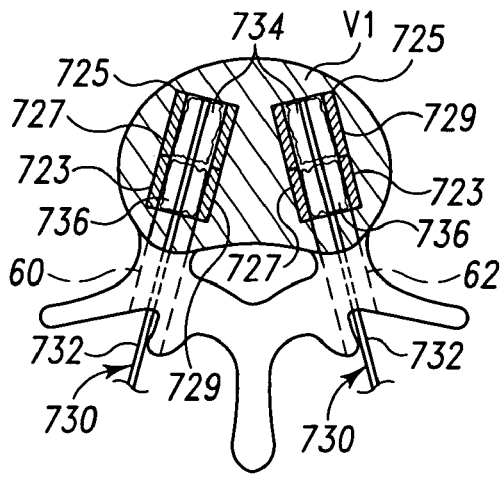
FIGS. 32A and 32B are a plan view and an elevation view in partial section, respectively, of collapsed expandable devices and delivery instruments according to another embodiment positioned in an intravertebral space of a vertebra.
Figure 32B:
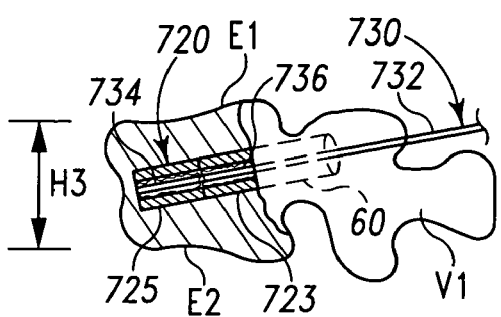

FIGS. 32A and 32B are a plan view and an elevation view in partial section, respectively, of another embodiment pair of collapsed expandable devices 720 and associated delivery instruments 730 positioned in an intravertebral space of vertebra V1. The collapsed or unexpanded expandable devices 720 are secured around the unexpanded expandable elements 734, 736 at a distal end of delivery instrument 730 for delivery to the intravertebral space. Expandable devices 720 each include a posterior portion 723 and an anterior portion 725, and a width between opposite sides 727, 729. The height and width of expandable devices 720 are substantially uniform in their collapsed or unexpanded condition along portions 723, 725.

Figure 33A:
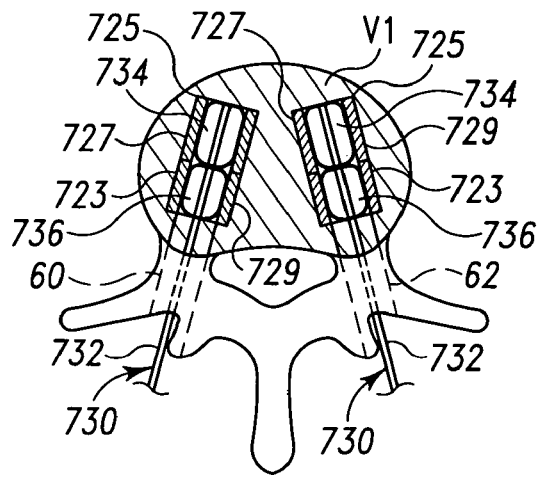
FIGS. 33A and 33B are a plan view and an elevation view in partial section, respectively, with expanded expandable devices and delivery instruments in the intravertebral space and the vertebra reduced.
Figure 33B:
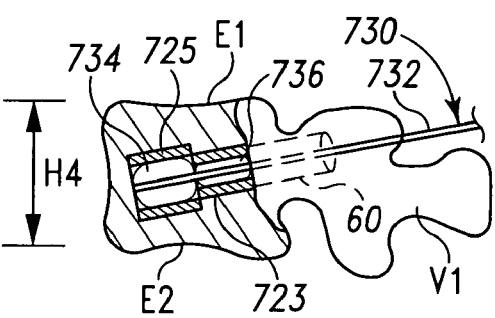

FIGS. 33A and 33B are a plan view and an elevation view in partial section, respectively, with expandable devices 720 expanded with a fluid delivered through shafts 732 of delivery instruments 730. In the expanded condition, posterior and anterior portions 723, 725 of expandable devices 720 compress cancellous bone and separate the opposite vertebral endplates E1, E2 to reduce vertebra V1 from compressed height H3 to provide a restored vertebral height H4. The width between opposite sides 727, 729 of expandable devices 720 remains substantially constant during and after expansion. Accordingly, expandable devices 720 are vertically expandable while their widths remain constant.

Expandable devices 720 are stepped in height between anterior portion 725 and posterior portion 723 to provide a greater anterior height for the expanded expandable devices 720. This stepped height provides a targeted reduction of vertebra V1 anteriorly where, for anterior fractures, the vertebral compression is greatest. To facilitate this stepped and targeted reduction, delivery instrument 730 can be provided with an anterior expandable element 734 and a posterior expandable element 736. Expandable elements 734, 736 can be provided with differing heights in their expanded configurations that conform to the expanded height of respective ones of the anterior and posterior portions 725, 723 in which expandable elements 734, 736 are positioned.

Figure 34A:
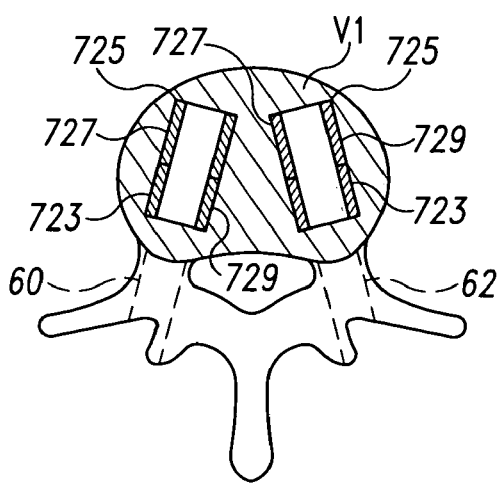
FIGS. 34A and 34B are a plan view and an elevation view in partial section, respectively, with expanded expandable devices in the intravertebral space of the reduced vertebra and the delivery instruments removed.
Figure 34B:
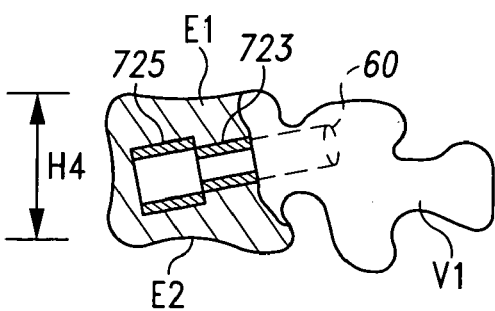

FIGS. 34A and 34B are a plan view and an elevation view in partial section, respectively, with the expanded expandable devices 720 in the reduced vertebra V1 of the spinal column segment and the delivery instruments 730 removed from cavities 726 of expandable devices 720. Filler material for bone growth can be placed in cavities 726 and in approaches 60, 62 as discussed above.

Figure 35A:
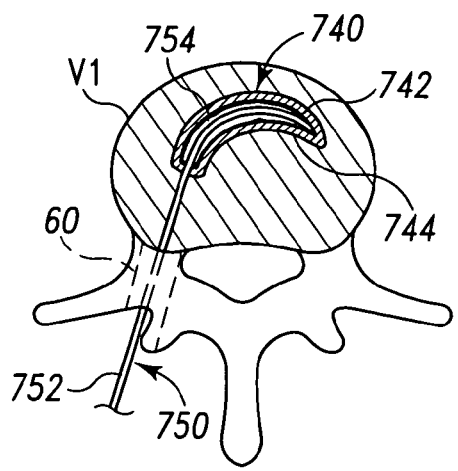
FIGS. 35A and 35B are a plan view and an elevation view in partial section, respectively, with a collapsed expandable device and delivery instrument according to another embodiment positioned in an intravertebral space of a vertebra.
Figure 35B:
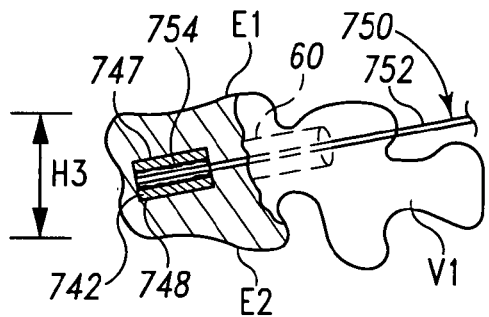

FIGS. 35A and 35B are a plan view and an elevation view in partial section, respectively, of another embodiment collapsed expandable device 740 and associated delivery instrument 750 positioned in a reduced height vertebra V1. The collapsed or unexpanded expandable device 740 is secured around the unexpanded expandable element 754 at a distal end of delivery instrument 750 for delivery to the reduced height vertebra V1. Expandable device 740 includes, in the collapsed condition, a convexly curved anterior wall 742 and a concavely curved posterior wall 744. Walls 742, 744 form a banana or kidney shape that facilitates placement of expandable device 740 in the intravertebral space for bi-lateral support of endplates E1, E2 of vertebra V1 from a single unilateral approach 60. Accordingly, the invasiveness of the procedure is even further reduced.

Figure 36A:
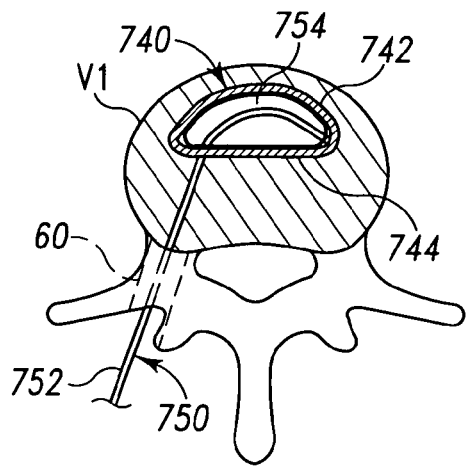
FIGS. 36A and 36B are a plan view and an elevation view in partial section, respectively, with the expanded expandable device and delivery instrument in the intravertebral space and the vertebra reduced.
Figure 36B:
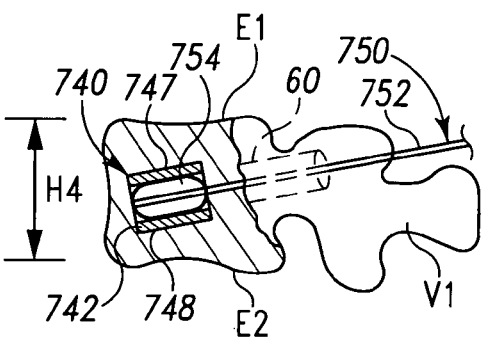

FIGS. 36A and 36B are a plan view and an elevation view in partial section, respectively, with expandable device 740 expanded with a fluid delivered through shaft 752 of delivery instrument 750. In the expanded condition, upper and lower portions 747, 748 of expandable device 740 compress the surrounding cancellous bone and separate the opposite vertebral endplates E1, E2 to reduce vertebra V1 to a restored height H4. Expansion of expandable device 740 can result in posterior wall 744 moving posteriorly such that in the expanded condition, posterior wall 744 is substantially linear to provide expandable device 740 with a D shape.

Expandable device 740 includes convexly curved anterior wall 742 which facilitates placement of expandable device 740 along a curved insertion path from approach 60 in which the anterior wall 742 conforms to the profile of the curved anterior portion of vertebra V1. In the illustrated embodiment, expandable device 740 is positioned in the anterior half of vertebra V1. Expandable element 754 can be provided with a shape that conforms to the D-shaped interior cavity 746 when expanded.

Figure 37A:
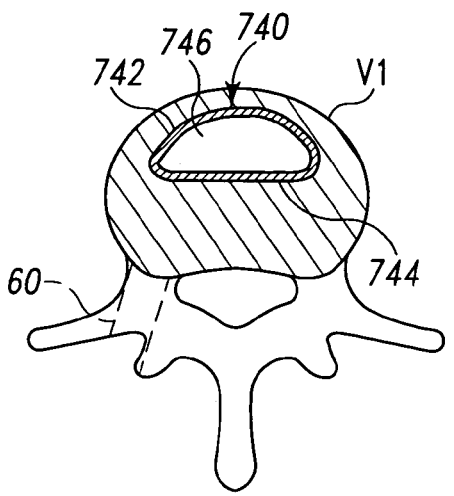
FIGS. 37A and 37B are a plan view and an elevation view in partial section, respectively, with the expanded expandable device in the intravertebral space of the reduced vertebra and the delivery instrument removed.
Figure 37B:
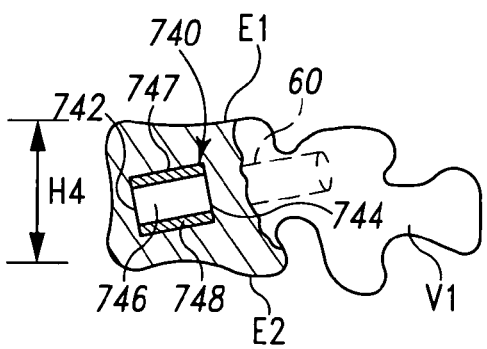

FIGS. 37A and 37B are a plan view and an elevation view in partial section, respectively, with the expanded expandable device 740 in the restored vertebra V1 of the spinal column segment and the delivery instrument 750 removed from cavity 746 of expandable device 740. Filler material for bone growth can be placed in cavity 746 and in approach 60 as discussed above.

Figure 38A:
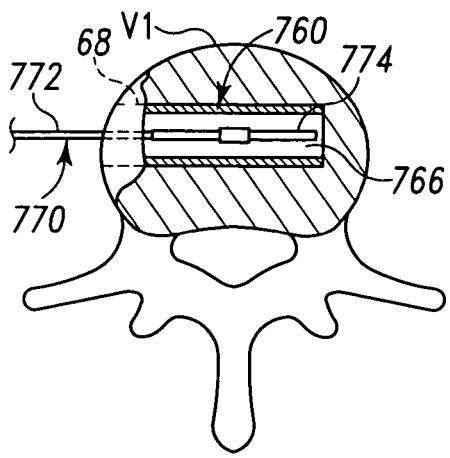
FIGS. 38A and 38B are a plan view and an elevation view in partial section, respectively, with a collapsed expandable device and delivery instrument according to another embodiment positioned in an intravertebral space of a vertebra.
Figure 38B:
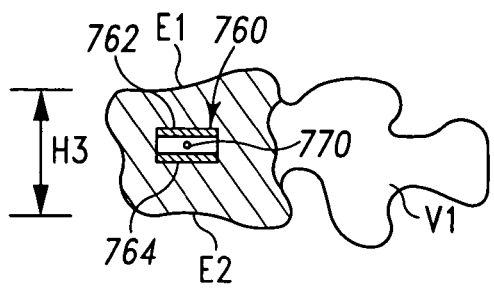

FIGS. 38A and 38B are a plan view and an elevation view in partial section, respectively, of another embodiment collapsed expandable device 760 and associated delivery instrument 770 positioned in a reduced height vertebra V1. The collapsed or unexpanded expandable device 760 is secured around the unexpanded expandable element 774 at a distal end of delivery instrument 770 for delivery to the intravertebral space from lateral approach 68. Expandable device 760 includes a first portion 762 and a second portion 764 engaged along opposite sides of expandable element 774 and positionable toward respective ones of the endplates E1 and E2.

Figure 39A:
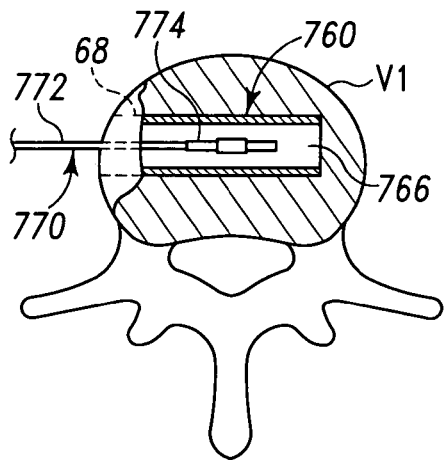
FIGS. 39A and 39B are a plan view and an elevation view in partial section, respectively, with the expanded expandable device and the delivery instrument in the intravertebral space and the vertebra reduced.
Figure 39B:
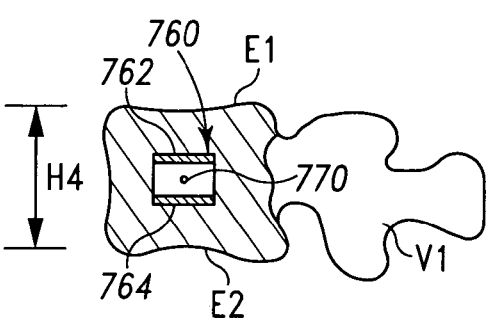

FIGS. 39A and 39B are a plan view and an elevation view in partial section, respectively, with expandable device 760 expanded by manipulating shaft 772 of delivery instrument 770 to expand expandable element 774. In the expanded condition, first and second portions 762, 764 of expandable device 760 compress the adjacent cancellous bone and separate opposite vertebral endplates E1, E2 to reduce vertebra V1 and provide a restored height H4.

Figure 40A:
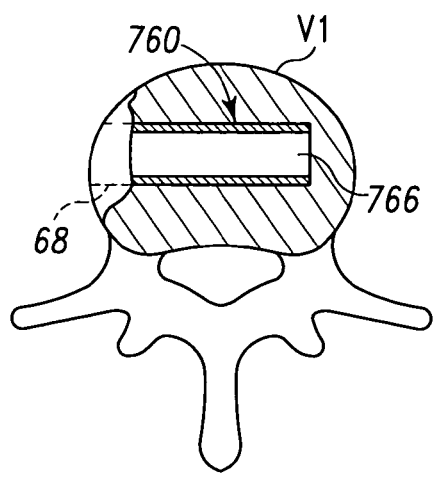
FIGS. 40A and 40B are a plan view and an elevation view in partial section, respectively, with the expanded expandable device in the intravertebral space of the reduced vertebra and the delivery instrument removed.
Figure 40B:
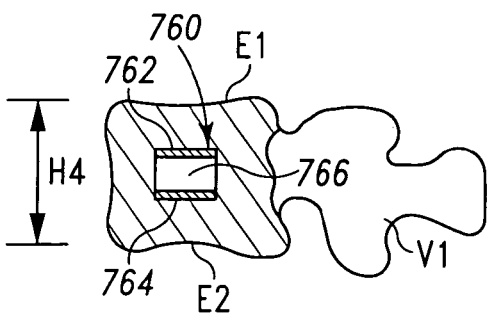

FIGS. 40A and 40B are a plan view and an elevation view in partial section, respectively, with the expanded expandable device 760 in the restored vertebra V1 of the spinal column segment and the delivery instrument 770 removed from cavity 766 of expandable device 760. Filler material for bone growth can be placed in cavity 766 and in approach 68 as discussed above.

Figure 41A:
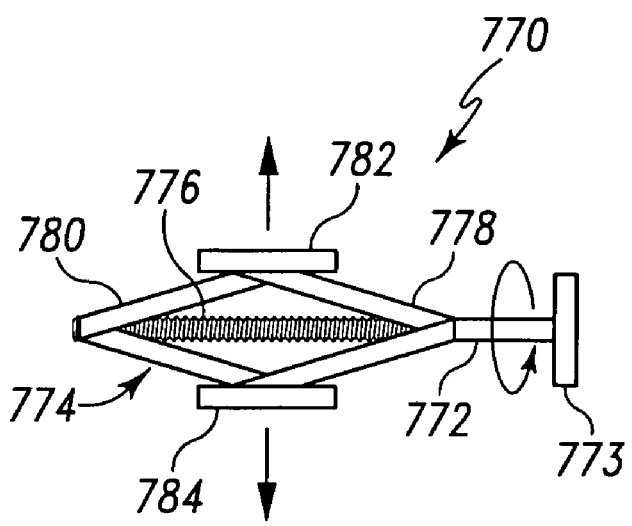
FIGS. 41A and 41B are elevational views of a delivery instrument with a distal expandable element in an unexpanded condition and expanded condition, respectively.
Figure 41B:
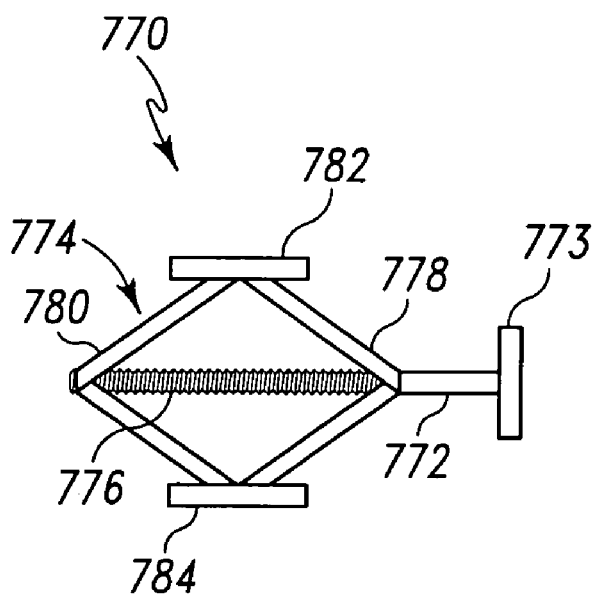

Further details of delivery instrument 770 are provided in FIGS. 41A and 41B. Shaft 772 includes a proximal handle portion 773 and a distal portion 776 extending through expandable element 774. Expandable element 774 includes a first pivoting linkage 778 and a second pivoting linkage 780. Linkages 778, 780 each include an intermediate pivot point engaged to and movable with distal portion 776. Linkages 778, 780 further include reduction members 782, 784 coupled at the upper and lower ends thereof.

Distal portion 776 is coupled to linkages 778, 780 so that, as shaft 772 is rotated about its axis with handle portion 773 as indicated in FIG. 41A, the pivoting intermediate portions of linkages 778, 780 are drawn toward one another to move reduction members 782, 784 away from one another, as shown in FIG. 41B. When positioned in a cavity of an expandable device, reduction members 782, 784 contact adjacent portions of the expandable device to expand the expandable device and reduce the vertebra. When the desired reduction has been achieved, expandable device 770 can be removed from the expandable device by rotating shaft 772 in the opposite direction and move reduction members 782, 784 toward one another.

The expandable devices herein can be provided with one or more openings, windows or other structure that allows communication between the interior cavity thereof and the adjacent bony tissue to facilitate bone ingrowth. The expandable devices can include a single cavity or multiple cavities. It is further contemplated that the expandable devices could be provided with support mechanisms positionable in the cavity to maintain or assist in maintaining an expanded condition of the device.

The expandable devices discussed herein can be made from any bio-compatible material, including metals, polymers and composites. Examples of metals include titanium and titanium alloys; nickel titanium alloys; stainless steel; and cobalt chrome alloys. Examples of polymers include polyaryletherketone; polyetherethereketone; polysulfone; polyolefin; polyethylene; tyrosine-based polycarbonate; polyester; polylactide; polyglicolide; polyorthoester; polyphosphazene; polyhydroxylbutyrate; and polyhydroxylvalerate, for example. Examples of composites include carbon filled composites; hydroxy-apetite filled composites; bioactive glass filled composites; and cortical bone chip filled composites, for example.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for intravertebral reduction, comprising:
   a delivery instrument including a radially expandable element along an outside surface of a distal portion thereof;
   an expandable device including a cavity, the expandable device being removably mountable to the expandable element with the expandable element in the cavity and each of the expandable device and the expandable element in an unexpanded condition, the expandable device including an external surface and an internal surface, said external surface having a first portion and a second portion movable away from one another upon expansion of the expandable element, the first portion defining a first linear outer surface and a second linear outer surface, the second portion defining a third linear outer surface and a fourth linear outer surface, said internal surface facing said cavity, wherein the expandable device is deliverable to an intravertebral space in the unexpanded condition and thereafter expandable with expansion of the expandable element to compress cancellous bone in the intravertebral space, wherein the first linear outer surface and the second linear outer surface define a first step, and the third linear outer surface and the fourth linear outer surface define a second step, such that the expandable device has a stepped cross-section configuration and such that in an expanded condition the first linear outer surface and the third linear outer surface are separated by a first height and the second linear outer surface and the fourth linear outer surface are separated by a second height greater than the first height; and bone filler material positioned in the cavity between the first and second portions.

2. The system of claim 1, wherein the expandable element includes a balloon structure with an interior for receiving an expansion fluid.

3. The system of claim 2, wherein the expansion fluid is selectable from the group consisting of: saline solution, compressed air, and radio-contrast fluid.

4. The system of claim 2, wherein the delivery instrument includes a shaft defining a lumen in fluid communication with the Interior of the expandable element, 5. The system of claim 1, wherein the first and second portions are uni-directionally movable away from one another upon expansion of the expandable element.

6. The system of claim 1, wherein the first and second portions are substantially rigid and the expandable element is non-rigid.

7. The system of claim 1, wherein the first and second portions are structured to maintain an expanded configuration after removal of the expandable element from the cavity therebetween.

8. The system of claim 1, wherein the bone filler material includes bone growth promoting material.

9. The system of claim 1, wherein the cavity opens at a distal and at a proximal end of the expandable device.

10. The system of claim 1, wherein said filler material Is bone growth material injected into said expandable element.

11. The system of claim 10, wherein said bone growth material causes said expansion of the expandable element and expansion of said expandable device.

12. The system of claim 1, wherein the first portion and the second portion are selectively movable relative to the other.

13. A system for intravertebral reduction, comprising:

a delivery instrument including a non-rigid radially expandable element along an outside surface of a distal portion thereof, an expandable device including a cavity between substantially rigid first and second portions, the expandable device being structured for positioning in an intravertebral space, wherein the expandable element is expandable in the cavity to move the first and second portions away from one another and compress cancellous bone in the intravertebral space, the first portion defining a linear anterior outer surface and a linear posterior outer surface, the second portion defining a linear anterior outer surface and a linear posterior outer surface, wherein the linear anterior outer surface and the linear posterior outer surface of the first portion define a first step, and the linear anterior outer surface and the linear posterior outer surface of the second portion define a second step, such that the expandable device has a stepped cross-section configuration such that in an expanded condition the linear anterior outer surface of the first portion and the linear anterior outer surface of the second portion are separated by a first height and the linear posterior outer surface of the first portion and the linear posterior outer surface of the second portion are separated by a second height greater than the first height; and bone filler material positioned in said expandable element in the cavity between the first and second portions.

14. The system of claim 13, wherein the first and second portions remain movably engaged with one another during expansion of the expandable element.

15. The system of claim 13, wherein the first and second portions are structured to maintain an expanded configuration after removal of the expandable element from the cavity therebetween.

16. The system of claim 13, wherein the expandable device is radially expandable.

17. The system of claim 13, wherein the expandable device includes a width between opposite sides thereof, the width remaining substantially constant in the unexpanded and expanded conditions.

18. The system of claim 13, wherein said expandable device includes an external surface and an internal surface, said internal surface facing said cavity, wherein no part of said external surface faces any part of said internal surface.

19. The system of claim 13, wherein the first portion and the second portion are selectively movable relative to the other.

20. A system for intravertebral reduction, comprising:

a delivery instrument including a radially expandable element along an outside surface of a distal portion thereof;

an expandable device including a cavity, the expandable device being removably mountable to the expandable element with the expandable element in the cavity and each of the expandable device and the expandable element in an unexpanded condition, the expandable device including a first surface facing generally toward said cavity, and a second surface facing generally away from said cavity, said second surface having a first portion and a second portion movable away from one another upon expansion of the expandable element, the first portions defining a first linear outer surface and a second linear outer surface, the second portion defining a third linear outer surface and a fourth linear outer surface, wherein the expandable device is deliverable to an intravertebral space in the unexpanded condition and thereafter expandable with expansion of the expandable element to compress cancellous bone in the intravertebral space, wherein the first linear outer surface and the second linear outer surface define a first step, and the third linear outer surface and the fourth linear outer surface define a second step, such that the expandable device has a stepped cross section configuration such that in an expanded condition the first linear outer surface of the first portion and the third linear outer surface of the second portion are separated by a first height and the second linear outer surface of the first portion and the fourth linear outer surface of the second portion are separated by a second height greater than the first height,
the first portion and the second portion being selectively movable relative to the other; and
filler material positioned in the cavity between the first and second portions.

* * * * *